(12) United States Patent
Chelak

(10) Patent No.: US 7,896,863 B2
(45) Date of Patent: Mar. 1, 2011

(54) POSITIVE DISPLACEMENT FLUID LOCK PORT

(75) Inventor: Todd M. Chelak, Westborough, MA (US)

(73) Assignee: Tyco Healthcare Group LP, Mansfield, MA (US)

( * ) Notice: Subject to any disclaimer, the term of this patent is extended or adjusted under 35 U.S.C. 154(b) by 61 days.

(21) Appl. No.: 12/141,178

(22) Filed: Jun. 18, 2008

(65) Prior Publication Data

US 2009/0005759 A1    Jan. 1, 2009

Related U.S. Application Data

(60) Provisional application No. 60/937,298, filed on Jun. 27, 2007.

(51) Int. Cl.
*A61M 25/16* (2006.01)
*A61M 25/18* (2006.01)
*A61M 5/14* (2006.01)
*F16L 37/28* (2006.01)

(52) U.S. Cl. ............... 604/533; 604/250; 251/149.6

(58) Field of Classification Search ............... 604/256, 604/167, 283, 246, 201, 203, 237, 244, 411, 604/415, 533; 251/149.1–149.7
See application file for complete search history.

(56) References Cited

U.S. PATENT DOCUMENTS

| | | | | |
|---|---|---|---|---|
| 1,477,573 A | * | 12/1923 | Lowrey | 285/114 |
| 2,092,400 A | * | 9/1937 | Miller | 251/7 |
| 2,526,630 A | * | 10/1950 | Bourke | 217/103 |
| 3,216,451 A | * | 11/1965 | Smallpeice | 137/861 |
| 4,063,708 A | * | 12/1977 | Smith | 251/149.4 |
| 4,557,024 A | * | 12/1985 | Roberts et al. | 24/20 TT |
| 4,917,668 A | | 4/1990 | Haindl | |
| 4,932,629 A | * | 6/1990 | Rodomista et al. | 251/4 |
| 5,069,424 A | * | 12/1991 | Dennany et al. | 251/149.6 |
| 5,439,451 A | | 8/1995 | Collinson et al. | |
| 5,549,651 A | | 8/1996 | Lynn | |
| 5,685,866 A | | 11/1997 | Lopez | |
| 5,694,686 A | | 12/1997 | Lopez | |
| 5,700,248 A | | 12/1997 | Lopez | |

(Continued)

FOREIGN PATENT DOCUMENTS

DE    38 09 127    4/1989

(Continued)

OTHER PUBLICATIONS

European Search Report from Application No. EP 08 25 2155 mailed Apr. 24, 2009.

*Primary Examiner*—Kevin C Sirmons
*Assistant Examiner*—William Carpenter
(74) *Attorney, Agent, or Firm*—Lisa E. Winsor, Esq.

(57) ABSTRACT

Positive displacement fluid lock ports for use in combination with an indwelling catheter and a syringe during a flushing/locking procedure are provided. The fluid lock port includes a housing having a distal and a proximal end; a resilient conduit supported within the housing, wherein the conduit defines a lumen therethrough; and at least one biasing member supported in the housing and being operatively associatable with the resilient conduit. The at least one biasing member has a first condition restrained from deforming the resilient conduit and a second condition operatively engaged with the resilient conduit to at least partially occlude the lumen of the resilient conduit.

9 Claims, 5 Drawing Sheets

U.S. PATENT DOCUMENTS

| | | |
|---|---|---|
| 5,776,116 A | 7/1998 | Lopez et al. |
| 5,873,862 A | 2/1999 | Lopez |
| 5,901,942 A | 5/1999 | Lopez |
| 5,928,204 A | 7/1999 | Lopez |
| 5,957,898 A | 9/1999 | Jepson et al. |
| 6,132,403 A | 10/2000 | Lopez |
| 6,132,404 A | 10/2000 | Lopez |
| RE37,357 E | 9/2001 | Lynn |
| 6,428,520 B1 * | 8/2002 | Lopez et al. ................ 604/249 |
| 6,572,592 B1 | 6/2003 | Lopez |
| 6,669,673 B2 | 12/2003 | Lopez |
| 6,682,509 B2 | 1/2004 | Lopez |
| 6,758,833 B2 | 7/2004 | Lopez |
| 6,840,501 B2 | 1/2005 | Doyle |
| 6,932,795 B2 | 8/2005 | Lopez et al. |
| 6,964,406 B2 | 11/2005 | Doyle |
| 7,104,520 B2 | 9/2006 | Leinsing et al. |
| RE39,334 E | 10/2006 | Lynn |
| 7,503,908 B2 | 3/2009 | Bartholomew |
| 7,510,545 B2 * | 3/2009 | Peppel ....................... 604/256 |
| 7,713,247 B2 | 5/2010 | Lopez |
| 7,713,248 B2 | 5/2010 | Lopez |
| 7,713,249 B2 | 5/2010 | Lopez |
| 7,717,883 B2 | 5/2010 | Lopez |
| 7,717,884 B2 | 5/2010 | Lopez |
| 7,717,885 B2 | 5/2010 | Lopez |
| 7,717,886 B2 | 5/2010 | Lopez |
| 7,717,887 B2 | 5/2010 | Lopez |
| 7,722,575 B2 | 5/2010 | Lopez |
| 7,722,576 B2 | 5/2010 | Lopez |
| 2002/0062106 A1 * | 5/2002 | Chu et al. ............. 604/167.01 |
| 2002/0147431 A1 | 10/2002 | Lopez et al. |
| 2004/0034329 A1 | 2/2004 | Mankus et al. |
| 2005/0154353 A1 | 7/2005 | Alheidt |
| 2006/0212006 A1 * | 9/2006 | Fangrow et al. ............. 604/284 |
| 2006/0247582 A1 | 11/2006 | Alheidt et al. |
| 2007/0093755 A1 | 4/2007 | Koos et al. |
| 2010/0059702 A1 | 3/2010 | Mansour et al. |
| 2010/0063482 A1 | 3/2010 | Mansour et al. |

FOREIGN PATENT DOCUMENTS

| | | |
|---|---|---|
| WO | WO 99/58186 | 11/1999 |

* cited by examiner

POSITIVE DISPLACEMENT FLUID LOCK PORT

CROSS-REFERENCE TO RELATED APPLICATION

The present application claims the benefit of and priority to U.S. Provisional Application Ser. No. 60/937,298, filed on Jun. 27, 2007, the entire content of which is incorporated herein by reference.

BACKGROUND

1. Technical Field

The present disclosure relates to fluid lock ports for use in flushing/locking procedures and, more particularly, to positive displacement fluid lock ports for use in combination with an indwelling catheter and a syringe during a flushing/locking procedure.

2. Background of Related Art

Numerous techniques are employed for the administration of "medical liquids" (e.g. liquid medication and flush/lock solutions) to a patient. In particular, where repeated medication infusions are required, medical liquids are often administered via the use of a vascular access catheter that is fluidly interconnected or interconnectable to one or more medical liquid sources via an associated tubing line set. Typically, the catheter is inserted into the vein of a patient and left there for multiple intravenous (IV) infusions during an extended course of medication therapy.

In conjunction with the repeated connection/disconnection of a vascular catheter and liquid medication source and tubing line set, it is usual practice to purge the vascular catheter with a flush solution (e.g. a saline solution) prior to and at the completion of a given liquid medication infusion. Pre-infusion flushing verifies that the vascular catheter is primed and clear of obstructions. Post infusion flushing/locking not only flushes through any remaining liquid medication to achieve the desired therapeutic effect, but also reduces any chance that the vascular catheter may become blocked in-between infusions, e.g. by a blood clot that may otherwise form in the vascular catheter.

A number of approaches are currently utilized for the noted flushing/locking procedures. Such techniques generally entail the usage of flush/lock solutions packaged in large volume, multi-dose reservoirs (e.g. about 250 ml. or more) or pre-filled unit dose syringes (e.g. having volumes of 2, 3, 5 or 10 ml.).

Flush/Lock procedures also require that care be taken to prevent blood reflux into the catheter. Reflux in I.V. therapy is the term commonly used to describe the fluid that is drawn back into the catheter after a flush/lock procedure. The concern is that the reflux fluid contains blood or solution that could cause the catheter to occlude. To ensure that reflux does not occur, flush/lock procedures suggest two techniques: 1) at the end of the flush/lock solution delivery, the user maintains pressure on the syringe plunger while clamping the I.V. line; or 2) while delivering the last 0.5 ml of flush/lock solution, disconnect the syringe from the I.V. port or clamp the I.V. line. Either technique maintains positive pressure on the fluid in the VAD to prevent reflux of fluid and blood.

For example, for hemodialysis procedures, catheters are commonly used for aspiration of blood for dialysis treatment and rapid return of the blood to circulation after treatment. In certain instances, a large bore venous line catheter may be required for the hemodialysis procedure. Catheters used for hemodialysis usually include two relatively large diameter lumens (usually molded as one catheter) for aspiration and rapid return of blood required during the hemodialysis procedure.

Catheter connections, such as, for example, connections of catheters to dialysis machine tubing, to IV line tubing, to infusion ports are most often made utilizing the medical industry's standardized Luer taper fittings. These fittings, which may either be male couplings or female couplings, include a tapered end of standardized dimensions. Coupling is made by the press-fit of mating parts. A threaded lock-fit or other type of securing mechanism is commonly utilized to ensure the integrity of the pressure fit of the Luer fittings.

A drawback of catheters is that, over time, a catheter can become occluded by a thrombus. In order to prevent clotting of catheters in blood vessels between uses such as, for example, between dialysis treatments when the catheter is essentially nonfunctioning and dwells inside a "central" vein (i.e. superior vena cava, inferior vena cava, iliac, etc), the lumens of the catheter are often filled with a lock solution that comprises a concentrated solution of the commonly used anticoagulant, heparin (up to 10,000 units of heparin per catheter lumen).

Following filling of the catheter with the lock solution, disconnection of the filling syringe from the catheter may result in some amount of drawback or reflux, i.e., wherein the catheter draws in some body fluid (e.g., blood), which may result in clotting thereof or the like.

It is desirable to have syringe assemblies and the like that are designed to minimize or reduce the incidents of reflux without depending entirely on user techniques.

Accordingly, there is a need for a device which helps to reduce or eliminate the incidents of reflux and which is independent of user technique.

SUMMARY

The present disclosure relates to positive displacement fluid lock ports for use in combination with an indwelling catheter and a syringe during a flushing/locking procedure.

According to an aspect of the present disclosure, a fluid lock port for inter-connection between a first medical device providing a flushing and/or locking fluid and a second medical device requiring a flushing and/or locking fluid is provided. The fluid lock port includes a housing having a distal and a proximal end; a resilient conduit supported within the housing, wherein the conduit defines a lumen therethrough; and at least one biasing member supported in the housing and being operatively associatable with the resilient conduit, wherein the at least one biasing member has a first condition restrained from deforming the resilient conduit and a second condition operatively engaged with the resilient conduit to at least partially occlude the lumen of the resilient conduit.

The at least one biasing member may be a resilient ring disposed about the resilient conduit. The resilient ring may include a substantially circular biased condition and a substantially ovular un-biased condition.

The housing may include a shoulder configured to support the resilient ring in the biased condition out of engagement with the resilient conduit.

The fluid lock port may further include at least one actuation member configured to move the resilient ring off of the shoulder of the housing and onto the resilient conduit. Each actuation member may be a pin slidably supported in the housing. Each actuation member may have a first condition in which each actuation member does not extend over the shoulder of the housing and a second condition in which each actuation member at least partially extends over the shoulder of the housing. Each actuation member may be configured for actuation upon connection of the housing to the first medical device.

The resilient ring may be prevented from movement from the first condition to the second condition by a portion of the first medical device that extends into the lumen of the resilient conduit. The resilient ring may be permitted to move to the second condition upon removal of the portion of the first medical device from within the lumen of the resilient conduit.

The biasing member may include a pair of biasing arms disposed on opposite sides of the resilient conduit. Each biasing arm may have a first biased condition out of engagement with the resilient conduit and a second unbiased condition wherein the pair of biasing arms operatively engage the resilient conduit to at least partially occlude the lumen of the resilient conduit therebetween.

The fluid lock port may further include at least one latch arm configured to retain each of the pair of biasing arms in the first biased condition. Each latch arm may be configured for actuation upon connection of the housing to the medical device providing at least one of the flushing and locking fluid. Each biasing arm may be prevented from movement from the first condition to the second condition by a portion of the first medical device that extends into the lumen of the resilient conduit. Each biasing arm may be permitted to move to the second condition upon removal of the portion of the first medical device from within the lumen of the resilient conduit.

The fluid lock port may further include a seal disposed across the lumen of the resilient conduit.

The at least partial occlusion of the lumen may result in a movement of fluid from a distal end of the second medical device.

The fluid lock port may be connectable to the first medical device prior to a connection to the second medical device.

According to another aspect of the present disclosure, a medical flushing and/or locking system is provided and includes a syringe having a nose; and a fluid lock port configured to selective connection to the syringe. The fluid lock portion includes a housing having a proximal end configured for selective coupling with the syringe; a resilient conduit supported within the housing wherein the conduit defines a lumen therethrough, wherein the nose of the syringe enters into the lumen of the resilient conduit when the fluid lock port is coupled to the syringe; and at least one biasing member supported in the housing and being operatively associatable with the resilient conduit, wherein the at least one biasing member has a first condition out of engagement with the resilient conduit and a second condition operatively engaged with the resilient conduit to at least partially occlude the lumen of the resilient conduit when the fluid lock port is uncoupled from the syringe.

The at least one biasing member may be a resilient ring disposed about the resilient conduit. The resilient ring may include a substantially circular biased condition and a substantially ovular un-biased condition.

The housing may include a shoulder configured to support the resilient ring in the biased condition. The medical flushing and/or locking system may further include at least one actuation member configured to move the resilient ring off of the shoulder of the housing and onto the resilient conduit.

Each actuation member may be a pin slidably supported in the housing. Each actuation member may have a first condition in which each actuation member does not extend over the shoulder of the housing and a second condition in which each actuation member extends over the shoulder of the housing. Each actuation member may be configured for actuation upon connection of the housing to the syringe.

The resilient ring may be prevented from movement from the biased condition to the un-biased condition by the nose of the syringe extending into the lumen of the resilient conduit. The resilient ring may be permitted to move to the un-biased condition upon removal of the nose of the syringe from within the lumen of the resilient conduit.

The medical flushing and/or locking system may further comprise a seal disposed across the lumen of the resilient conduit. The at least partial occlusion of the lumen may result in a movement of fluid from a distal end of the resilient conduit.

According to a further aspect of the present disclosure, a fluid lock port for inter-connection between a first medical device providing a flushing and/or locking fluid and a second medical device requiring a flushing and/or locking fluid is provided. The fluid lock port includes a housing being configured for selective fluid connection at one end to the first medical device and at a second end to the second medical device, the housing containing a resilient conduit which can establish fluid communication between the first and second medical devices, and including a biasing member restrained from deforming the conduit while the housing is connected to the first medical device. The fluid lock port is configured to create a positive displacement of the flushing and/or locking fluid during a disconnection of the first medical device which removes restraint from the biasing member thereby causing deformation of the conduit.

The fluid lock port may be connectable to the first medical device prior to a connection to the second medical device.

DETAILED DESCRIPTION OF THE DRAWINGS

Various embodiments of the presently disclosed fluid lock ports are disclosed herein with reference to the drawings, wherein.

Figure 7:
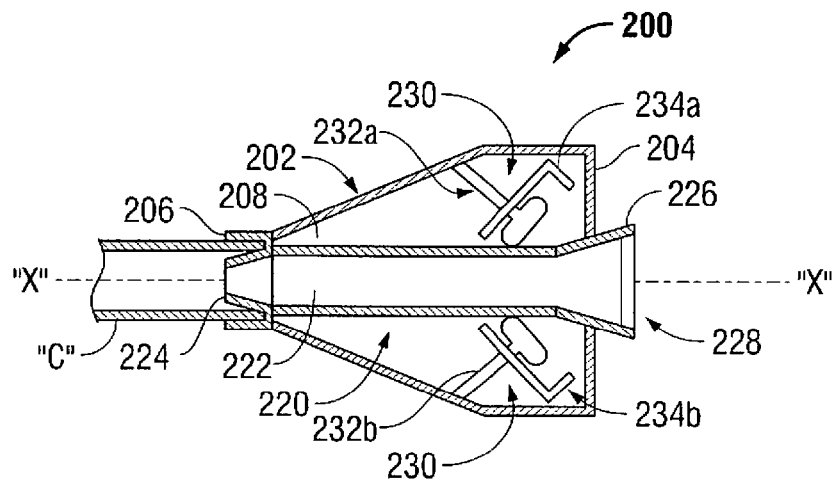
FIG. 7 is a schematic, longitudinal, cross-sectional, side elevational view of a fluid lock port according to another embodiment of the present disclosure, shown in a first condition.
Figure 8:
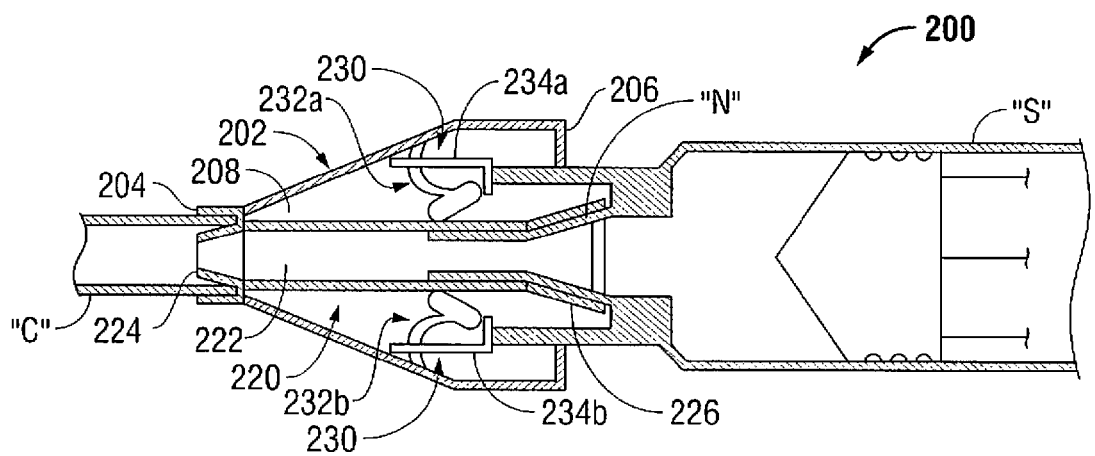
FIG. 8 is a schematic, longitudinal, cross-sectional, side elevational view of the fluid lock port of FIG. 7, shown in a second condition, following attachment of a syringe thereto.
Figure 9:
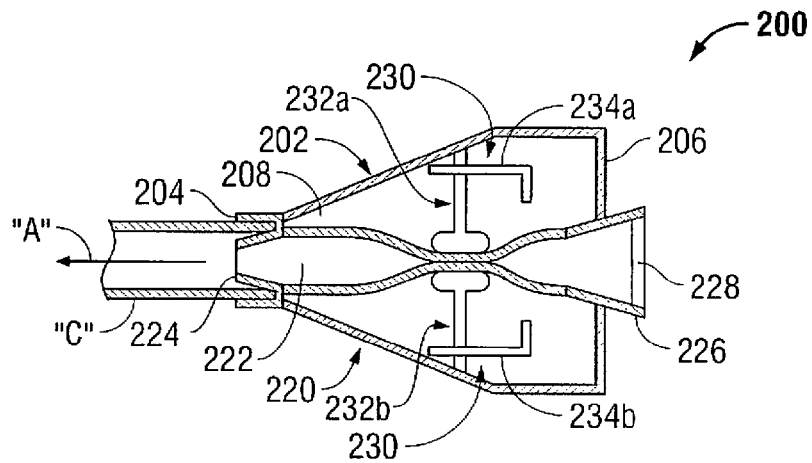
Figure 10:
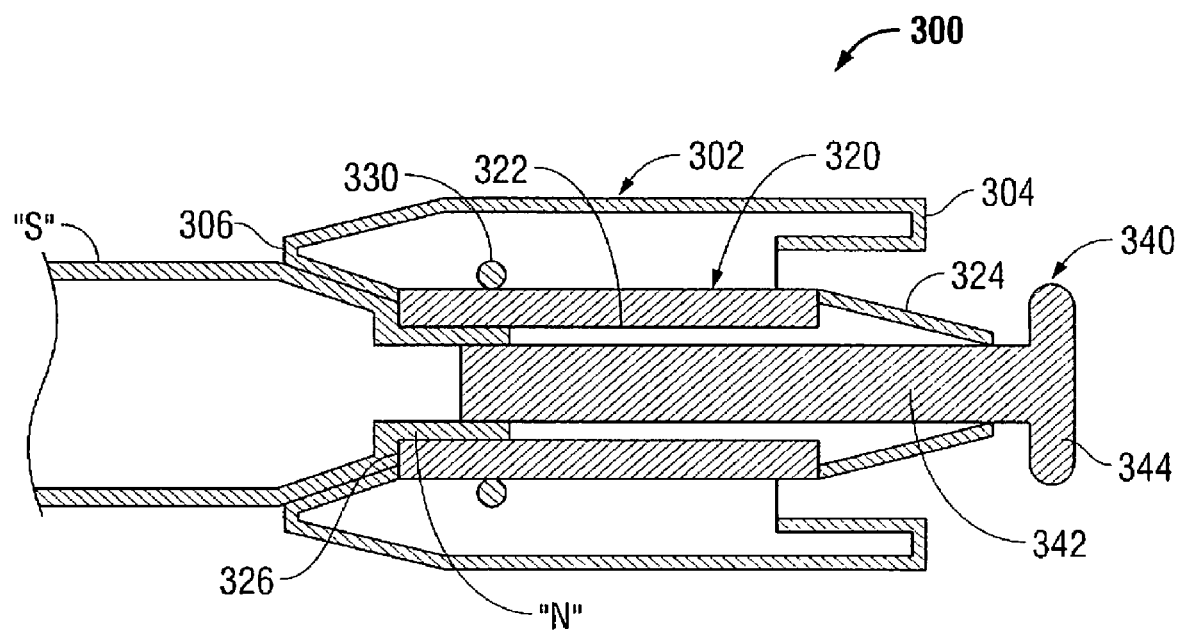
Figure 11:
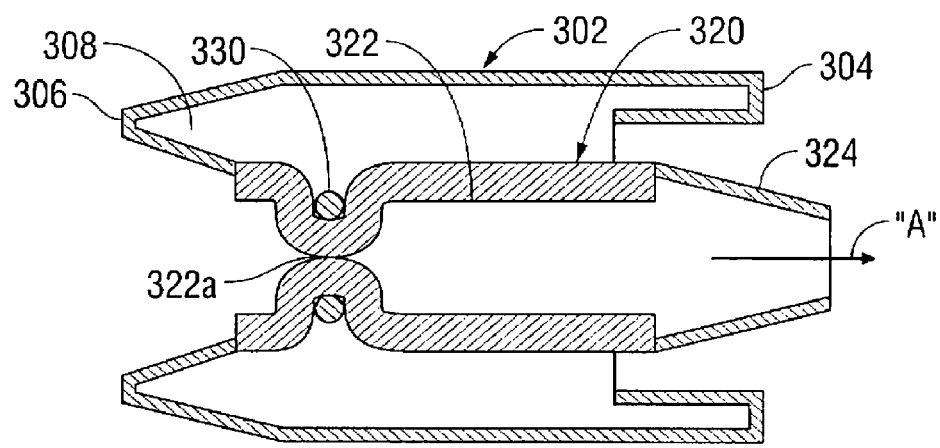

FIG. 9 is a schematic, longitudinal, cross-sectional, side elevational view of the fluid lock port of FIGS. 7 and 8, shown in a third condition, following detachment of the syringe therefrom; and FIG. 10 is a schematic, longitudinal, cross-sectional, side elevational view of a fluid lock port according to another embodiment of the present disclosure, shown operatively connected to a syringe; and FIG. 11 is a schematic, longitudinal, cross-sectional, side elevational view of the fluid lock port of FIG. 10, shown disconnected from the syringe.

DETAILED DESCRIPTION OF EMBODIMENTS

Embodiments of the presently disclosed fluid lock ports will now be described in detail with reference to the drawings wherein like reference numerals designate identical or corresponding elements in each of the several views.

In this description, the term proximal is generally used to indicate relative nearness of a referenced item to a user of the device and the term distal is used to indicate relative remoteness of a referenced item to a user of the device.

Figure 1:
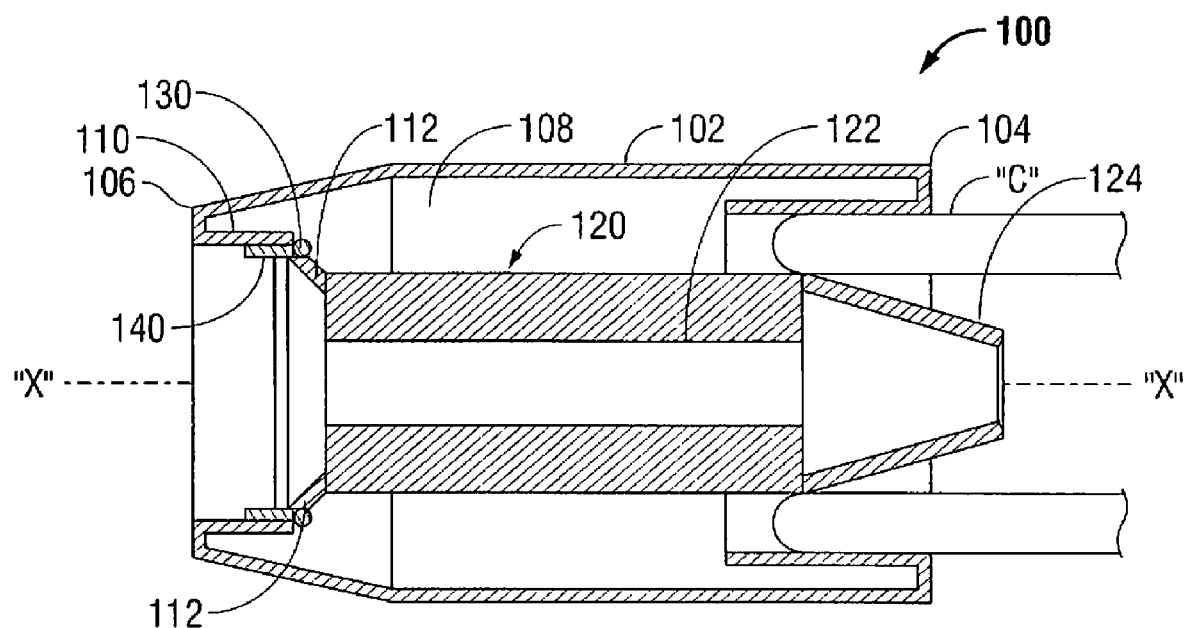
FIG. 1 is a longitudinal cross-sectional, side elevational view of a fluid lock port according to an embodiment of the present disclosure, shown in a first condition.
Figure 2:
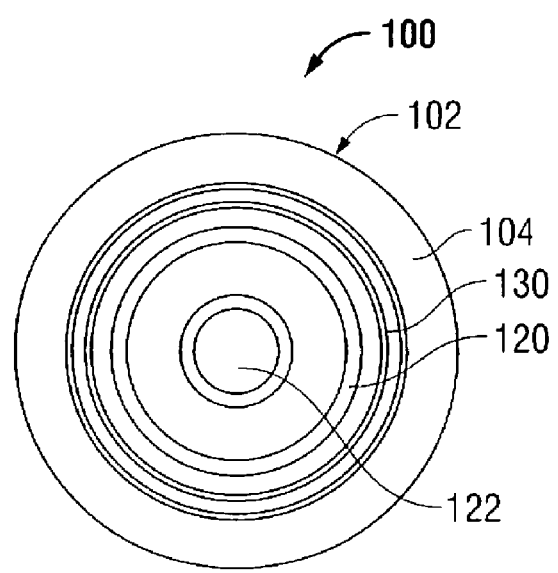
FIG. 2 is a front, elevational view of the fluid lock port of FIG. 1.

Referring initially to FIGS. 1 and 2, a fluid lock port, in accordance with an embodiment of the present disclosure, is generally designated as 100. As seen in FIGS. 1 and 2, fluid lock port 100 is shown in a first condition or stage wherein a lumen extending therethrough is open or patent.

As seen in FIGS. 1 and 2, fluid lock port 100 includes a housing 102 having a distal end 104, a proximal end 106 and defining a cavity or chamber 108 therein. Housing 102 may have a substantially cylindrical shape or configuration. Housing 102 includes an annular flange or wall 110 extending from proximal end 106 thereof and in the direction of cavity 108. Annular wall 110 terminates in a shoulder or ledge 112 at one end and in a distal tip 124 at the other end.

Housing 102 may be constructed from a suitably rigid or substantially rigid material, such as, for example, polycarbonate, polypropylene or high density polyurethane.

Fluid lock port 100 further includes a conduit or tube 120 extending from annular wall 110, in the direction of cavity 108 and defines a lumen 122 therethrough. Conduit 120 defines a longitudinal central axis "X" which is co-axial with a longitudinal central axis of housing 102. Conduit 120 terminates in a tapered distal tip 124 which is configured for easier connection with a complementary connector of a medical access device, such as, for example, an I.V. catheter, valve or the like "C".

Conduit 120 may be constructed from a suitably flexible and/or resilient material such as elastomers or, more preferably, thermoplastic elastomers including styrene block copolymers, polyolefin blends, elastomeric alloys, thermoplastic polyurethanes, thermoplastic copolyester and thermoplastic polyamides. Preferably, housing 102 is molded in at least two pieces which are assembled together with conduit 120 during manufacture of lock port 100.

Figure 6:
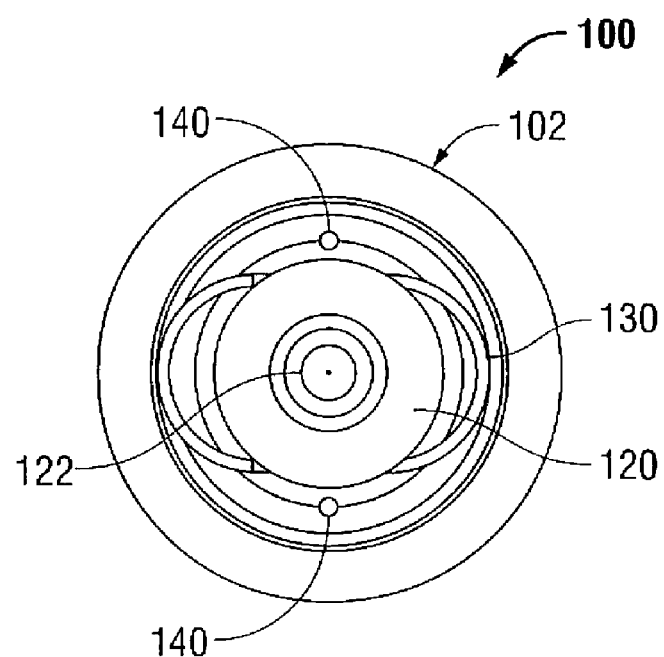
FIG. 6 is a front, elevational view of the fluid lock port of FIG. 5.

Fluid lock port 100 further includes a biasing member 130 disposed about shoulder 112 of annular wall 110 and/or conduit 120. As seen in FIG. 2, biasing member 130 may be in the form of a loop having a substantially circular profile when in a biased condition when positioned about shoulder 112 of annular wall 110 and, as seen in FIG. 6, a substantially ovular or non-circular profile when in an unbiased condition when positioned about conduit 120. Biasing member 130 may have a substantially circular transverse cross-sectional profile.

Biasing member 130 may be fabricated from a suitable resilient material, such as, for example, spring steel, nickel-titanium and its alloys, or the like.

Fluid lock port 100 further includes at least one latch pin 140 (a pair of latch pins 140 being shown in FIGS. 1 and 3-6). Latch pins 140 are slidably supported on or in shoulder 112 of annular wall 110 such that a longitudinal axis thereof is substantially parallel with the longitudinal central axis "X" of conduit 120. Latch pins 140 have a first position in which latch pins 140 do not extend distally beyond shoulder 112 of annular wall 110 or do not interfere with biasing member 130 resting on shoulder 112 of annular wall 110, and at least a second position in which latch pins 140 extend at least partially across shoulder 112 of annular wall 110 to prevent/inhibit biasing member 130 from resting on shoulder 112 of annular wall 110.

It is contemplated that distal end 104 and/or proximal end 106 of housing 102 may include suitable inter-engagement elements, such as, for example, taper 124 of conduit 120, formed therein or therewith which are configured and adapted to mate with corresponding engagement elements of intended medical devices, such as, for example, syringes, valves, catheters and the like.

Turning now to FIGS. 1-6, a detailed discussion of the use and/or operation of fluid lock port 100 is shown and described. As seen in FIGS. 1 and 2, fluid lock port 100 has an initial condition or configuration in which latch pins 140 are in the first position, biasing member 130 is supported on shoulder 112 of annular wall 110 in its first condition out of engagement with conduit 120, and lumen 122 of conduit 120 is open or patent because biasing member 130 is restrained from deforming conduit 120. Fluid lock port 100 may be connected to a suitable valve, catheter or the like "C" via distal end 124 of conduit 120.

Figure 3:
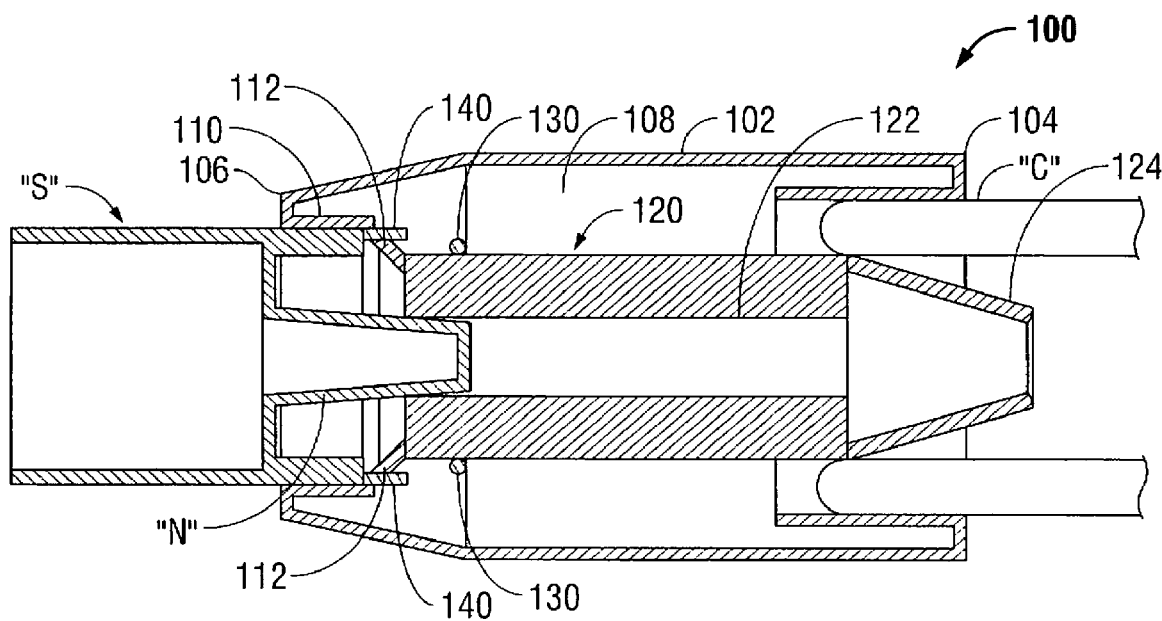
FIG. 3 is a longitudinal cross-sectional, side elevational view of a fluid lock port of FIGS. 1 and 2, shown in a second condition, following attachment of a syringe thereto.
Figure 4:
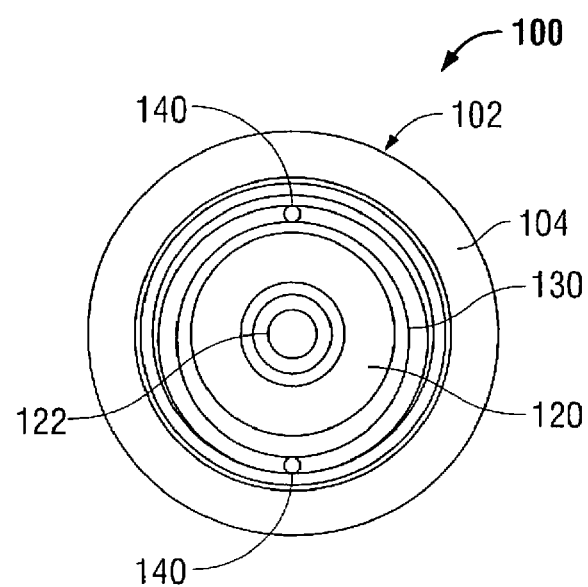
FIG. 4 is a front, elevational view of the fluid lock port of FIG. 3.

As seen in FIGS. 3 and 4, as a syringe "S" or other medical device is connected to proximal end 106 of housing 102, a nose "N" thereof is introduced into lumen 122 of conduit 120. Nose "N" of syringe preferably has a length sufficient to extend distally beyond shoulder 112 of annular wall 100. As syringe "S" is connected to housing 102, a distal surface of syringe "S" presses against latch pins 140 thereby moving latch pins 140 from the first position to the second position. In so doing, latch pins 140 urge or move biasing member 130 off of shoulder 112 of annular wall 100. With biasing member 130 dislodged off of shoulder 112 of annular wall 110, biasing member 130 seeks to achieve its second or unbiased condition.

However, as seen in FIGS. 3 and 4, biasing member 130 substantially comes to rest on conduit 120 in a region overlying the portion of nose "N" of syringe "S" which extends into lumen 122 of conduit 120; the slope of shoulder 112 can be designed to guide the biasing member 130 to an appropriate second position. Accordingly, nose "N" of syringe "S" continues to maintain biasing member 130 substantially in its first condition or in a substantially biased condition even though biasing member 130 is resting at the second position.

Moreover, lumen 122 of conduit 120 is maintained open or patent thereby allowing for fluids and the like to be delivered therethrough. Such fluids include and are not limited to a saline, a lock solution and the like. As used herein, the term "lock solution" refers to a solution that is injected or otherwise infused into a lumen of a catheter with the intention of allowing a substantial portion of the lock solution to remain in the lumen and not in the systemic blood circulation until it is desired or required to access that particular lumen again, typically for additional treatment, i.e., infusion or withdrawal of fluid.

Suitable lock solutions include an anticoagulant, many of which are well known to those skilled in the art, including, for example and without limitation, citrate, heparin, urokinase, tissue plasminogen activation (tPA) and mixtures of these agents. As described in International Application No. PCT/US00/15177 entitled A CATHETER LOCK SOLUTION INCLUDING A PHOTO-OXIDANT, filed May 10, 2001, the lock solution can also include a photo-oxidant. The solution can also include a variety of additional materials, such as, for example, an antibacterial or antimicrobial agent. Such antibacterial and antimicrobial agents are well known to those skilled in the art and can include, for example and without limitation, gentamicin, vancomycin, and mixtures of these agents.

Figure 5:
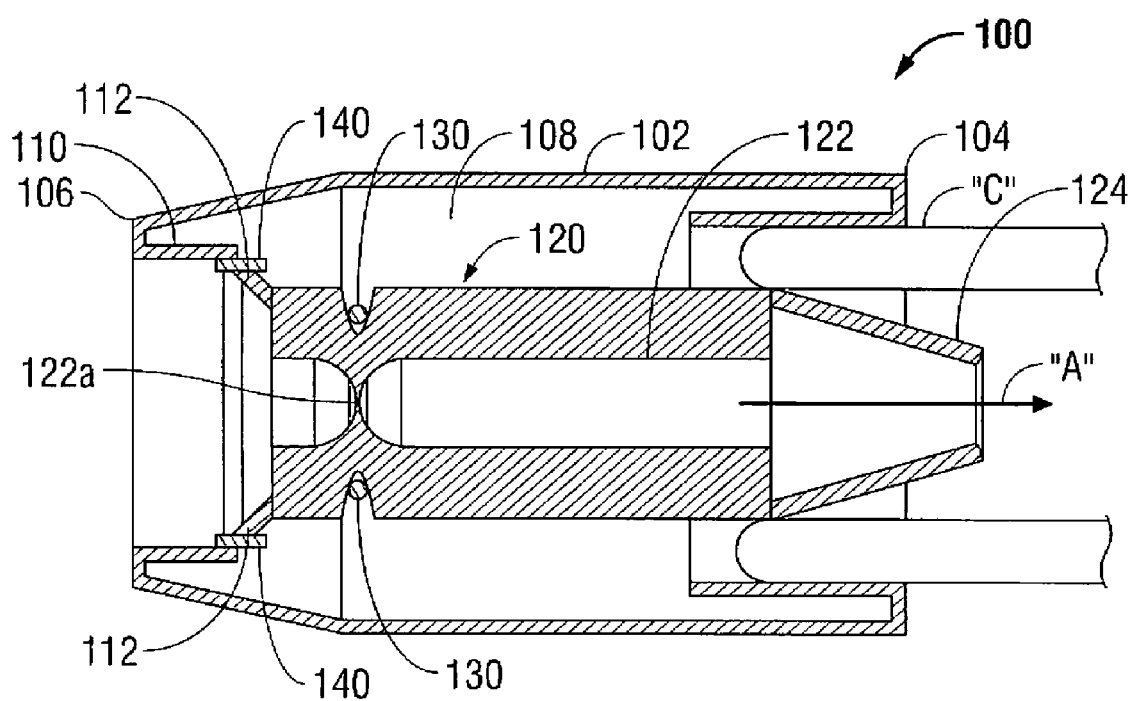
FIG. 5 is a longitudinal cross-sectional, side elevational view of a fluid lock port of FIGS. 1-4, shown in a third condition, following detachment of the syringe therefrom.

As seen in FIGS. 5 and 6, when syringe "S" is disconnected from fluid lock port 100, nose "N" thereof is withdrawn from within lumen 122 of conduit 120, biasing member 130 is free to return to a second or unbiased condition thereof, thereby constricting or pinching conduit 120 and occluding or blocking lumen 122 thereof. Upon the return of biasing member 130 to the second or unbiased condition, the compressive-type energy exerted upon conduit 120, by biasing member 130 attempting to achieve its unbiased condition, is sufficient to result in the collapsing or flattening of conduit 120. This constriction or flattening of conduit 120 achieves a degree of distal or positive displacement of the fluid contained within lumen 122 of conduit 120, resulting in a movement of the fluid out of a distal end of the catheter "C", as indicated by arrow "A".

Since biasing member 130 has yet to achieve its fully unbiased condition at this stage, biasing member 130 is capable of locking/clamping lumen 122 of conduit 120.

Turning now to FIGS. 7-9, a fluid lock port according to an alternate embodiment of the present disclosure is generally designated 200. Fluid lock port 200 is substantially similar to fluid lock port 100 and thus will only be described in detail herein to the extent necessary to identify differences in construction and operation.

As seen in FIGS. 7-9, fluid lock port 200 includes a housing 202 having a distal end 204, a proximal end 206 and defining a cavity or chamber 208 therein. Housing 202 may be constructed from a suitably rigid or substantially rigid material, such as, for example, polycarbonate, polypropylene or high density polyurethane.

Fluid lock port 200 further includes a conduit or tube 220 extending through chamber 208 and defining a lumen 222 therethrough. Conduit 220 defines a longitudinal central axis "X" which is co-axial with a longitudinal central axis of housing 202. Conduit 220 includes a tapered distal tip 224 which is configured for easier connection with a complementary connector of a medical access device, such as, for example, an I.V. catheter, valve or the like "C". Conduit 220 includes a proximal end 226 configured to receive a nose "N" of a syringe "S" or the like. Proximal end 226 of conduit 220 may extend proximally beyond proximal end 206 of housing 202.

Conduit 220 may be constructed from a suitably flexible and/or resilient material, such as, for example, polyvinylchloride (PVC) or low density polyurethane.

Conduit 220 may include a seal 228 extending across proximal end 226 thereof. Seal 228 may be in the form of a septum seal or any other seal member suitable for the intended purpose of occluding lumen 222 of conduit 220.

Fluid lock port 200 further includes a conduit biasing mechanism 230 supported within cavity 208 of housing 202. Conduit biasing mechanism 230 may include a pair of opposed biasing members 232a, 232b supported in housing 202. Each biasing member 232a, 232b may be in the form of a resilient arm or the like having a biased condition, spaced a distance from conduit 220, and an unbiased condition in contact with conduit 220. Biasing member 232a, 232b are supported in housing 202 such that when biasing member 232a, 232b are in the unbiased condition biasing member 232a, 232b occlude, constrict or pinch conduit 220 therebetween, as will be described in greater detail below.

Biasing members 232a, 232b may be fabricated from any suitable resilient material capable of transmitting a sufficient force to conduit 220 so as to occlude, constrict or pinch conduit 220 when biasing members 232a, 232b are in the unbiased condition. Biasing members 232a, 232b may be fabricated from a suitable resilient material, such as, for example, spring steel, nickel-titanium and its alloys, or the like.

Conduit biasing mechanism 230 further includes a pair of latch arms 234a, 234b each supported in housing 202 and each being configured to selectively engage respective biasing member 232a, 232b. Each latch arm 234a, 234b has a first condition operatively engaged with a respective biasing member 232a, 232b, for maintaining biasing members 232a, 232b in the biased condition, and a second condition operatively disengaged from a respective biasing member 232a, 232b for enabling the biasing members 232a, 232b to return to the unbiased condition.

Each latch arm 234a, 234b is configured such that, upon attachment of fluid lock port 200 to a syringe "S" or the like (see FIG. 8), latch arms 234a, 234b are actuated from the first condition to the second condition.

It is contemplated that distal end 204 and/or proximal end 206 of housing 202 may include suitable inter-engagement elements, such as, for example, tapered distal tip 224 and/or seal 228, formed therein or therewith which are configured and adapted to mate with corresponding engagement elements of intended medical devices, such as, for example, syringes, valves, catheters and the like.

Turning now to FIGS. 7-9, a detailed discussion of the use and/or operation of fluid lock port 200 is shown and described. As seen in FIG. 7, fluid lock port 200 has an initial condition or configuration in which latch arms 234a, 234b are in the first condition, biasing members 232a, 232b are supported by latch arms 234a, 234b in the first condition, and lumen 222 of conduit 220 is open or patent. Fluid lock port 200 may be connected to a suitable valve, catheter or the like "C" via distal end 224 of conduit 220.

As seen in FIG. 8, as a syringe "S" or other medical device is connected to proximal end 206 of housing 202, a nose "N" thereof is introduced into lumen 222 of conduit 220. Nose "N" of syringe preferably has a length sufficient to extend distally beyond biasing members 232a, 232b of conduit biasing mechanism 230, when biasing members 232a, 232b are in the biased condition. Also, as syringe "S" is connected to fluid lock port 200, nose "N" enters into conduit 220 through seal 228. In this manner, seal 228 conforms around nose "N" of syringe "S" to form a fluid tight seal therewith.

Additionally, as syringe "S" is connected to housing 202, a distal surface of syringe "S" presses against latch arms 234a, 234b thereby moving latch arms 234a, 234b from the first condition to the second condition.

In so doing, latch arms 234a, 234b disengage from biasing members 232a, 232b allowing for biasing members 232a, 232b to move from the first condition to the second condition due to un-biasing of biasing members 232a, 232b. With biasing members 232a, 232b disengaged from latch arms 234a, 234b, biasing members 232a, 232b seek to achieve their second or unbiased condition.

However, as seen in FIG. 8, biasing members 232a, 232b substantially come to rest on conduit 220 in a region overlying the portion of nose "N" of syringe "S" which extends into lumen 222 of conduit 220. Accordingly, nose "N" of syringe "S" maintains biasing members 232a, 232b substantially in their first condition. Moreover, lumen 222 of conduit 220 is maintained open or patent thereby allowing for fluids and the like (e.g., saline, lock solution, etc.) to be delivered therethrough.

As seen in FIG. 9, when syringe "S" is disconnected from fluid lock port 200, nose "N" thereof is withdrawn from within lumen 222 of conduit 220, biasing members 232a, 232b are free to return to a second or unbiased condition thereof, thereby constricting or pinching conduit 220 and occluding or blocking lumen 222 thereof. Upon the return of biasing members 232a, 232b to the second or unbiased condition, the compressive-type energy exerted upon conduit 220, by biasing members 232a, 232b attempting to achieve its unbiased condition, is sufficient to result in the collapsing or flattening of conduit 220. This constriction or flattening of conduit 220 achieves a degree of distal or positive displacement of the fluid contained within lumen 222 of conduit 220, resulting in a movement of the fluid out of a distal end of the catheter "C", as indicated by arrow "A".

Since biasing members 232a, 232b have yet to achieve their fully unbiased condition at this stage, biasing members 232a, 232b are capable of locking/clamping lumen 222 of conduit 220.

Turning now to FIGS. 10 and 11, a fluid lock port according to an alternate embodiment of the present disclosure is generally designated 300. Fluid lock port 300 is substantially similar to fluid lock port 100 and thus will only be described in detail herein to the extent necessary to identify differences in construction and operation.

As seen in FIGS. 10 and 11, fluid lock port 300 includes a housing 302 having a distal end 304, a proximal end 306 and defining a cavity or chamber 308 therein. Housing 302 may be constructed from a suitably rigid or substantially rigid material such as, for example, polycarbonate, polypropylene or high density polyurethane.

Fluid lock port 300 further includes a conduit or tube 320 extending through chamber 308 and defining a lumen 322 therethrough. Conduit 320 includes a tapered distal tip 324 which is configured for easier connection with a complementary connector of a medical access device, such as, for example, an I.V. catheter, valve (not shown) or the like "C". Conduit 320 includes a proximal end 326 configured to receive a nose "N" of a syringe "S" or the like.

Conduit 320 may be constructed from a suitably flexible and/or resilient material, such as elastomers or, more preferably, thermoplastic elastomers including styrene block copolymers, polyolefin blends, elastomeric alloys, thermoplastic polyurethanes, thermoplastic copolyester and thermoplastic polyamides. Preferably, housing 302 is molded in at least two pieces which are assembled together with conduit 320 during manufacture of lock port 300.

Fluid lock port 300 further includes a biasing member 330 disposed about conduit 320, preferably about a proximal portion thereof. Biasing member 330 may be substantially similar to biasing member 130 and thus reference may be made to the discussion of biasing member 130 for a detailed discussion of biasing member 330.

Fluid lock port 300 is connected to or supported on a distal end of a syringe "S" in such a manner that nose "N" of syringe "S" extends into lumen 322 of conduit 320. Nose "N" of syringe "S" extends a distance sufficient to extend distally beyond at least adjacent to the location of biasing member 330. In this manner, biasing member 330 is maintained in a biased condition by the nose "N" of syringe "S" so that biasing member 330 is restrained from deforming conduit 120, thereby preventing conduit 320 from pinching or crimping.

Fluid lock port 300 further includes a cap or pin 340 disposed within lumen 322 of conduit 320. Cap 340 includes a body portion 342 extending through lumen 322 of conduit 320 and optionally into nose "N" of syringe "S". Cap 340 includes a head portion 344 at a distal end of body portion 342 which is configured to prevent cap 340 from entering completely into lumen 322 of conduit 320 and for providing a user with an engagement portion for removal of cap 340 from within conduit 320.

In this embodiment (as seen in FIG. 10), cap 340 would function to occlude nose "N" of syringe "S" and seal the fluid within syringe "S" during storage.

With continued reference to FIGS. 10 and 11, a detailed discussion of the use and/or operation of fluid lock port 300 is shown and described. As seen in FIG. 10, fluid lock port 300 is pre-attached to a nose "N" of a syringe "S" and has an initial condition or configuration in which nose "N" of syringe "S" extends into lumen 322 of conduit 320, body portion 342 of cap 340 extends through lumen 322 of conduit 320 such that an end of body portion 342 is supported in nose "N" of syringe "S", and biasing member 330 is supported on conduit 320 at a location overlying that portion of nose "N" of syringe "S" extending into lumen 322 of conduit 320.

In use, cap 340 is detached from fluid lock port 300 and syringe "S". In so doing, lumen 322 of conduit 320 is opened. Distal end 306 of housing 302 may then be connected to a suitable valve, catheter or the like "C" (see FIGS. 1-6).

Following use of syringe "S", as seen in FIG. 11, when syringe "S" is disconnected from fluid lock port 300, nose "N" thereof is withdrawn from within lumen 322 of conduit 320, biasing member 330 is free to return to a second or unbiased condition thereof, thereby constricting or pinching conduit 320 and occluding or blocking lumen 322 thereof. Upon the return of biasing member 330 to the second or unbiased condition, the compressive-type energy exerted upon conduit 320, by biasing member 330 attempting to achieve its unbiased condition, is sufficient to result in the collapsing or flattening of conduit 320. This constriction or flattening of conduit 320 achieves a degree of distal or positive displacement of the fluid contained within lumen 322 of conduit 320, resulting in a movement of the fluid out of lumen 322 of conduit 320, as indicated by arrow "A".

Since biasing member 330 has yet to achieve its fully unbiased condition at this stage, biasing member 330 is capable of locking/clamping lumen 322 of conduit 320.

In accordance with the present disclosure, a medical flushing/locking system may be provided. The flushing/locking system may include a syringe configured to dispense a fluid, as is known in the art. The flushing/locking system may further include any of fluid lock ports 100, 200, 300 disclosed herein.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

What is claimed is:

1. A fluid lock port for inter-connection between a first medical device providing a flushing and/or locking fluid and a second medical device requiring a flushing and/or locking fluid, the fluid lock port comprising:
   a housing having a distal and a proximal end;
   a resilient conduit supported within the housing, wherein the conduit defines a lumen therethrough;
   at least one biasing member supported in the housing and being operatively associatable with the resilient conduit, wherein the at least one biasing member has a first condition restrained from deforming the resilient conduit and a second condition operatively engaged with the resilient conduit to at least partially occlude the lumen of the resilient conduit;

wherein the at least one biasing member is a resilient ring disposed about the resilient conduit, wherein the resilient ring includes a substantially circular biased condition and a substantially oval un-biased condition; and wherein the housing includes a shoulder configured to support the resilient ring in the biased condition out of engagement with the resilient conduit; and at least one actuation member configured to move the resilient ring off of the shoulder of the housing and onto the resilient conduit, wherein each actuation member is a pin slidably supported in the housing, wherein each one actuation member has a first condition in which each actuation member does not extend over the shoulder of the housing and a second condition in which each one actuation member at least partially extends over the shoulder of the housing.

2. The fluid lock port according to claim 1, wherein each actuation member is configured for actuation upon connection of the housing to the first medical device.

3. The fluid lock port according to claim 1, wherein the resilient ring is prevented from movement from the first condition to the second condition by a portion of the first medical device that extends into the lumen of the resilient conduit, and wherein the resilient ring is permitted to move to the second condition upon removal of the portion of the first medical device from within the lumen of the resilient conduit.

4. The fluid lock port according to claim 1, wherein each latch arm is configured for actuation upon connection of the housing to the medical device providing at least one of the flushing and locking fluid.

5. The fluid lock port according to claim 1, further comprising a seal disposed across the lumen of the resilient conduit.

6. The fluid lock port according to claim 1, wherein the at least partial occlusion of the lumen results in a movement of fluid from a distal end of the second medical device.

7. The fluid lock port according to claim 1, wherein the fluid lock port is connectable to the first medical device prior to a connection to the second medical device.

8. A fluid lock port for inter-connection between a first medical device providing a flushing and/or locking fluid and a second medical device requiring a flushing and/or locking fluid, the fluid lock port comprising:

a housing being configured for selective fluid connection at one end to the first medical device and at a second end to the second medical device, the housing containing a resilient conduit which can establish fluid communication between the first and second medical devices, and including a biasing member restrained from deforming the conduit while the housing is connected to the first medical device;

wherein each biasing member is a resilient ring disposed about the resilient conduit, wherein the resilient ring includes a substantially circular biased condition and a substantially oval un-biased condition; and wherein the housing includes a shoulder configured to support the resilient ring in the biased condition out of engagement with the resilient conduit; and at least one actuation member configured to move the resilient ring off of the shoulder of the housing and onto the resilient conduit, wherein each actuation member is a pin slidably supported in the housing, wherein each actuation member has a first condition in which each actuation member does not extend over the shoulder of the housing and a second condition in which each actuation member at least partially extends over the shoulder of the housing;

wherein the fluid lock port is configured to create a positive displacement of the flushing and/or locking fluid during a disconnection of the first medical device which removes restraint from the biasing member thereby causing deformation of the conduit.

9. The fluid lock port according to claim 8, wherein the fluid lock port is connectable to the first medical device prior to a connection to the second medical device.

* * * * *